(12) United States Patent
Bush et al.

(10) Patent No.: US 11,160,901 B2
(45) Date of Patent: Nov. 2, 2021

(54) BIOADHESIVE CHITOSAN GEL FOR CONTROLLING BLEEDING AND FOR PROMOTING HEALING WITH SCAR REDUCTION WITHOUT OBSCURING OR INTERFERING WITH ACCESS TO A SURGICAL FIELD

(71) Applicant: Tricol Biomedical, Inc., Portland, OR (US)

(72) Inventors: Maggie Bush, Kansas City, MO (US); Sam Kuhn, Portland, OR (US); Simon McCarthy, Portland, OR (US)

(73) Assignee: TRICOL BIOMEDICAL, INC., Portland, OR (US)

( * ) Notice: Subject to any disclaimer, the term of this patent is extended or adjusted under 35 U.S.C. 154(b) by 0 days.

(21) Appl. No.: 15/565,388

(22) PCT Filed: Apr. 11, 2016

(86) PCT No.: PCT/US2016/026939
§ 371 (c)(1),
(2) Date: Oct. 9, 2017

(87) PCT Pub. No.: WO2016/164903
PCT Pub. Date: Oct. 13, 2016

(65) Prior Publication Data
US 2018/0110897 A1 Apr. 26, 2018

Related U.S. Application Data

(60) Provisional application No. 62/145,958, filed on Apr. 10, 2015.

(51) Int. Cl.
| | | |
|---|---|---|
| *A61L 24/08* | (2006.01) | |
| *A61L 24/00* | (2006.01) | |
| *C08L 5/08* | (2006.01) | |
| *A61K 47/36* | (2006.01) | |
| *A61K 47/10* | (2017.01) | |
| *A61K 31/155* | (2006.01) | |
| *A61K 47/14* | (2017.01) | |
| *A61K 47/02* | (2006.01) | |
| *A61K 31/785* | (2006.01) | |
| *A61K 47/12* | (2006.01) | |
| *A61K 9/06* | (2006.01) | |

(52) U.S. Cl.
CPC ............ *A61L 24/08* (2013.01); *A61K 9/06* (2013.01); *A61K 31/155* (2013.01); *A61K 31/785* (2013.01); *A61K 47/02* (2013.01); *A61K 47/10* (2013.01); *A61K 47/12* (2013.01); *A61K 47/14* (2013.01); *A61K 47/36* (2013.01); *A61L 24/0031* (2013.01); *A61L 24/0042* (2013.01); *C08L 5/08* (2013.01); *A61L 2400/04* (2013.01)

(58) Field of Classification Search
CPC .... A61K 47/12; A61K 31/155; A61K 31/785; A61K 47/02; A61K 47/10; A61K 47/14; A61K 47/36; A61K 9/06; A61L 24/08; A61L 2400/04; A61L 24/0031; A61L 24/0042; C08L 5/08
See application file for complete search history.

(56) References Cited

U.S. PATENT DOCUMENTS

| | | | |
|---|---|---|---|
| 7,371,403 B2 | 5/2008 | McCarthy et al. | |
| 9,925,210 B2 | 3/2018 | McCarthy et al. | |
| 2005/0196497 A1 | 9/2005 | Soedjak et al. | |
| 2007/0036867 A1* | 2/2007 | Mohapatra | A61K 9/146 424/489 |
| 2009/0004122 A1 | 1/2009 | Modak et al. | |
| 2009/0117213 A1 | 5/2009 | Beaulieu et al. | |
| 2011/0171311 A1* | 7/2011 | Gousse | A61L 27/20 424/488 |
| 2012/0252755 A1 | 10/2012 | Henco et al. | |
| 2013/0164311 A1 | 6/2013 | DeCarlo et al. | |
| 2013/0165402 A1 | 6/2013 | Dvorak et al. | |
| 2014/0275291 A1 | 9/2014 | McGrath et al. | |
| 2015/0216894 A1 | 8/2015 | McCarthy et al. | |
| 2018/0169134 A1 | 6/2018 | McCarthy et al. | |

FOREIGN PATENT DOCUMENTS

| | | | |
|---|---|---|---|
| CA | 2134635 A1 | 5/1995 | |
| KR | 20120033393 A * | 4/2012 | ............... A61K 8/02 |
| WO | 01/41820 A1 | 6/2001 | |

OTHER PUBLICATIONS

English machine translation of Choi (KR-10-2012-0033393 A; published Apr. 9, 2012) made Nov. 9, 2018. (Year: 2018).*
Isbrucker et al., "Risk and safety assessment on the consumption of Licorice root (*Glycyrrhiza* sp.), its extract and powder as a food ingredient, with emphasis on the pharmacology and toxicology of glycyrrhizin", 2006, Regulatory Toxicology and Pharmacology, vol. 46, pp. 167-192. (Year: 2006).*
English machine translation of KR-10-2012-0033393 A made Mar. 26, 2019; pp. 1-10. (Year: 2019).*
Desai et al., "Study of Gamma-Irradiation Effects on Chitosan Microparticles," *Drug Delivery* 13(1):39-50, 2006.
Khokhlova et al., "Chitosan nanostructures deposited from solutions in carbonic acid on a model substrate as resolved by AFM," *Colloid and Polymer Science* 290(15):1471-1480, 2012.

(Continued)

*Primary Examiner* — Michael B. Pallay
(74) *Attorney, Agent, or Firm* — Seed IP Law Group LLP (57) ABSTRACT

An aqueous chitosan gel system of novel non-scarring, non-interfering, transparent, stable, solubilized chitosan that controls bleeding is described herein. The aqueous chitosan gel system can comprise water, chitosan, an acid, a plasticizer, a rheology modifying agent, an antioxidant stabilizer, an alcohol, and a multi-valent salt. Additional components of the aqueous chitosan gel system can comprise a bifunctional organic acid, a tnfunctional organic acid, a multifunctional organic acid, a phosphoric acid, a polyphosphoric acid and a salt.

30 Claims, 2 Drawing Sheets

(56) References Cited

OTHER PUBLICATIONS

Liu et al., "A chitosan-arginine conjugate as a novel anticoagulation biomaterial," *Journal of Materials Science: Materials in Medicine* 15(11):1199-1203, 2004.
"Carbonic Acid," Wikipedia, URL=http://en.wikipedia.org/w/index.php?title=Carbonic_acid&oldid=643507-228, Jan. 21, 2015, 7 pages.
Berscht et al., "In vitro evaluation of biocompatibility of different wound dressing materials," *Journal of Materials Science: Materials in Medicine* 6(4):201-205, 1995.
Bugten et al., "Effects of Nonabsorbable Packing in Middle Meatus after Sinus Surgery," *The Laryngoscope* 116(1):83-88, 2006.
Butler, *Carbon Dioxide Equilibria and Their Applications*, Lewis Publishers, Chelsea, Michigan, USA, 1991, pp. 1-73. (42 pages).
Cafaggi et al., "Preparation and evaluation of chitosan salt-poloxamer 407 based matrix for buccal drug delivery," *Journal of Controlled Release* 102(1):159-169, 2005.
Chandra et al., "Advantages and disadvantages of topical packing in endoscopic sinus surgery," *Current Opinion in Otolaryngology & Head and Neck Surgery* 12(1):21-26, 2004.
Chandra et al., "Long-Term Effects of FloSeal™ Packing After Endoscopic Sinus Surgery," *American Journal of Rhinology* 19(3):240-243, 2005.
Chandra et al., "The Effect of FloSeal on Mucosal Healing after Endoscopic Sinus Surgery: A Comparison with Thrombin-Soaked Gelatin Foam," *American Journal of Rhinology* 17(1):51-55, 2003.
Foster, "Bioadhesives as Surgical Sealants: A Review," Chapter 9 in Bianco-Peled et al. (eds.), *Bioadhesion and Biomimetics: From Nature to Applications*, CRC Press, Boca Raton, Florida, USA, 2015, pp. 203-234.
Frenkiel et al., "Use of Hylan B Gel as a Wound Dressing after Endoscopic Sinus Surgery," *The Journal of Otolaryngology* 31(Supplement 1):S41-S44, 2002.
Gallyamov et al., "Collagen tissue treated with chitosan solutions in carbonic acid for improved biological prosthetic heart valves," *Materials Science and Engineering: C* 37:127-140, 2014.
Gorczyca et al., "Preparation and characterization of genipin cross-linked porous chitosan-collagen-gelatin scaffolds using chitosan-$CO_2$ solution," *Carbohydrate Polymers* 102:901-911, 2014.
Grabovac et al., "Comparison of the mucoadhesive properties of various polymers," *Advanced Drug Delivery Reviews* 57(11):1713-1723, 2005.
He et al., "Preparation of chitosan films using different neutralizing solutions to improve endothelial cell compatibility," *Journal of Materials Science: Materials in Medicine* 22(12):2791-2802, 2011.
Hobbs, *Ice Physics*, Oxford University Press, London, England, 1974, Chapter 9, "Growth of ice from the liquid phase," pp. 575-629. (31 pages).
Huggins, "Control of Hemorrhage in Otorhinolaryngologic Surgery with Oxidized Regenerated Cellulose," *The Eye, Ear, Nose and Throat Monthly* 48(7):420-423, 1969.
Johnson et al., "In Vivo Tissue Response to Implanted Chitosan Glutamate," in Brine et al. (eds.), *Advances in Chitin and Chitosan*, Elsevier Science Publishers, London, England, 1992, 8 pages.
Karkos et al., "Day-case endoscopic sinus surgery using dissolvable haemostatic nasal packs: a pilot study," *European Archives of Otorhinolaryngology* 264(10):1171-1174, 2007.

Lee et al., "Synthesis and characterization of a chitosan derivative," *The FASEB Journal* 28(Supplement 1), 2014, 2 pages. (Abstract).
Levi et al., "Bidirectional Relation Between Inflammation and Coagulation," *Circulation* 109(22):2698-2704, 2004.
Levi et al., "Two-Way Interactions Between Inflammation and Coagulation," *Trends in Cardiovascular Medicine* 15(7):254-259, 2005.
Maccabee et al., "Effects of Topically Applied Biomaterials on Paranasal Sinus Mucosal Healing," *American Journal of Rhinology* 17(4):203-207, 2003.
MacKenzie, "The Physico-Chemical Basis for the Freeze-Drying Process," *Developments in Biological Standardization* 36:51-67, 1976.
Miya et al., "I.r. spectroscopic determination of CONH content in highly deacylated chitosan," *International Journal of Biological Macromolecules* 2(5):323-324, 1980.
Ogle et al., "Surgery of the Nose and Paranasal Sinuses: Principles and Concepts," *Oral & Maxillofacial Surgery Clinics of North America* 24(2):xiii-xiv, 2012.
Palmer et al., "Endoscopic Surgery of the Nose and Paranasal Sinus," *Oral & Maxillofacial Surgery Clinics of North America* 24(2):275-283, 2012.
Pomerantz et al., "Platelet Gel for Endoscopic Sinus Surgery," *Annals of Otology, Rhinology & Laryngology* 114(9):699-704, 2005.
Sakai et al., "A Novel Method of Dissolving Chitosan in Water for Industrial Application," *Polymer Journal* 33(8):640-642, 2001.
Sakai et al., "Chitosan-Coating of Cellulosic Materials Using an Aqueous Chitosan-$CO_2$ Solution," *Polymer Journal* 34(3):144-148, 2002.
Shaw et al., "Effect of packing on nasal mucosa of sheep," *The Journal of Laryngology & Otology* 114(7):506-509, 2000.
Shepherd et al., "Chitosan functional properties," *Glycoconjugate Journal* 14(4):535-542, 1997.
Sigurdsson et al., "Assessment of mucoadhesion by a resonant mirror biosensor," *International Journal of Pharmaceutics* 325(1-2):75-81, 2006.
Tang et al., "Antibacterial action of a novel functionalized chitosan-arginine against Gram-negative bacteria," *Acta Biomaterialia* 6(7):2562-2571, 2010.
Valentine et al., "Advances in Absorbable Biomaterials and Nasal Packing," *Otolaryngologic Clinics of North America* 42(5):813-828, 2009.
Virgin et al., "Evolving Materials and Techniques for Endoscopic Sinus Surgery," *Otolaryngologic Clinics of North America* 43(3):653-672, 2010.
Von Schoenberg et al., "Nasal packing after routine nasal surgery—is it justified?" *The Journal of Laryngology and Otology* 107(10):902-905, 1993.
West et al. (eds.), "Electrical Conductivity of Aqueous Solutions," *CRC Handbook of Chemistry and Physics*, 70th ed., CRC Press, Boca Raton, Florida, USA, 1989, 1 page.
Woodworth et al., "A gelatin-thrombin matrix for hemostasis after endoscopic sinus surgery," *American Journal of Otolaryngology—Head and Neck Medicine and Surgery* 30(1):49-53, 2009.
Wormald et al., "A prospective single-blind randomized controlled study of use of hyaluronic acid nasal packs in patients after endoscopic sinus surgery," *American Journal of Rhinology* 20(1):7-10, 2006.

* cited by examiner

FIG. 1

Rates of bleeding control for Synaero, Chitosan Gel A, Chitosan Gel B and Merogel

FIG. 2

Stability shelf-life 23±2 °C trend-line for Chitosan Gel C viscosity based on zeroth order hydrolytic degradation

BIOADHESIVE CHITOSAN GEL FOR CONTROLLING BLEEDING AND FOR PROMOTING HEALING WITH SCAR REDUCTION WITHOUT OBSCURING OR INTERFERING WITH ACCESS TO A SURGICAL FIELD

RELATED APPLICATIONS

This application claims priority to U.S. provisional application Ser. No. 62/145,958, filed on Apr. 10, 2015, titled BIOADHESIVE CHITOSAN GEL FOR CONTROLLING BLEEDING AND FOR PROMOTING HEALING WITH SCAR REDUCTION WITHOUT OBSCURING OR INTERFERING WITH ACCESS TO A SURGICAL FIELD. The entire contents of the above-referenced application is incorporated by reference herein and made part of this specification.

FIELD OF THE INVENTION

This invention relates to aqueous chitosan and chitosan derivative gel systems of novel non-scarring, non-interfering, transparent, stable, solubilized chitosan that controls bleeding.

BACKGROUND OF THE INVENTION

If there is bleeding into surgical field, visibility of the field can be limited to the extent that surgery must halt until bleeding stops and the field becomes visible again. This can result in significantly extended surgery time with significantly increased surgery cost. In some cases, disruption of surgical field visibility directly results in inability to perform a surgical procedure.

Thermal cautery and suction have become the mainstays of bleeding control and maintaining surgical field visibility in general surgery. Cautery is effective in controlling moderate levels of oozing bleeding but results in increased incidence of scarring and adhesions. Tissue damage associated with cautery presents as fibrosis and scarring. It is desirable that hemostatic techniques other than cautery should be considered in surgeries where delicate tissue is involved or where scarring is not acceptable. Such surgeries include those of the ear, nose and throat (ENT), general reconstructive, general plastic, maxillofacial, neurological, vascular, oncological resection and gynecological.

Functional endoscopic sinus surgery (FESS) [1-4], is used to achieve sinus enlargement and to remove obstructing tissue and/or undesirable tissue growth from the sinus passage. Removal of vascularized tissue from the passageway results in a moderate to robust bleeding. Cautery use is kept at a minimum because of risk of associated scarring. Hemostatic packing [5-9] may be used to control bleeding, however packing placement occludes the passageway, causing disruption of the surgical procedure. Packing removal often leads to postoperative bleeding and more delay. Hemostatic gel systems [10-18] are available; however they suffer from difficulties that are addressed by this invention disclosure. These difficulties include gel system instability, insufficient hemostatic efficacy [13, 16], interference with access to and visualization of the surgical site [10, 11, 13, 16, 17], promotion of scarring [10, 11, 14-17], and concern with antibody formation and disease transmission in the case of biologic agents [10, 11, 14-16]. Agents that provide effective hemostasis by strong direct interaction with the intrinsic clotting cascade have been found to cause adverse adhesions and scarring on wound healing [19, 20].

Chitosan is produced at the industrial level by hydrolytic deacetylation of chitin. Chitin and chitosan are part of the glycosaminoglycan family of polymers. Chitosan is typically derived from chitin by deacetylation in the presence of alkali. Chitosan is a generic term used to describe linear polysaccharides which are composed of glucosamine and N-acetyl glucosamine residues joined by β-(1-4) glycosidic linkages (typically the number of glucosamines≥N-acetyl glucosamines) and whose composition is soluble in dilute aqueous acid. The chitosan family encompasses poly-β-(1-4)-N-acetyl-glucosamine and poly-β-(1-4)-N-glucosamine with the acetyl residue fraction and its motif decoration (either random or block) affecting chitosan chemistry. The 2-carbon amino group on the glucosamine ring in chitosan allows for protonation, and hence solubilization of chitosan in water (pKa≈6.5) (Roberts). This allows the ready processing of chitosan into fibers, films, and other forms, as well as the ability to prepare high purity chitosan for biomedical use.

The derivatization of chitosan most often involves derivatization of the glucosamine C-2 nitrogen with an electrophile, however it may also involve reaction of the C-6 alcohol of the glucosamine or N-acetyl glucosamine. The derivatization of chitosan may involve glucosamine C-2 covalent bonding in which N-acetyl, N-formyl, N-acetyl, N-chloroacetyl, N-ethyl, N-propyl, N-propionyl, N-isopropyl, N-(2-methylproprionyl), N-hydroxyethyl, N-succinyl, N-pentanoyl, N-carboxy, N-carboxymethyl, N-butyryl, N-(2,2-dimethylpropionyl), N-(3-methylbutyryl), N-(3,3-dimethylbutyryl), N-sulfonyl, N,N-dicarboxymethyl, N-butyl, N-pentyl and/or N-hexyl acyl modifications might be made to chitosan to achieve similar effect. Other generic chemical modifications involving nucleophile/electrophile reaction of the glucosamine C-2 nitrogen or C-6 alcohol of glucosamine or N-acetyl-glucosamine would include N-alkylation, N-alkylidene/N-arylidene derivitization, and metal chelation.

The term "chitosan" as used in the compositions of the present invention refers to chitosan or its derivatives that is, at least initially, soluble in an aqueous solution having a pH below or at about 6.5. It is noted that the chitosan included in the compositions of the present invention may at some point become insoluble, but that the insoluble material is nonetheless continuously referred to as chitosan throughout this disclosure based on its initial solubility in an aqueous solution having a pH below or at about 6.5. Accordingly, disclosed herein are inventive compositions which comprise chitosan and that may or may not, at some point, include an insoluble chitosan material.

SUMMARY OF THE INVENTION

An aqueous chitosan gel system of novel non-scarring, non-interfering, transparent, stable, solubilized chitosan that controls bleeding is described herein. According to the invention the aqueous chitosan gel system is provided: comprising water, chitosan, an acid, a plasticizer, a rheology modifying agent, an antioxidant stabilizer an alcohol and a multi-valent salt. Additional components may comprise a bifunctional organic acid, a trifunctional organic acid, a multi-functional organic acid, a phosphoric acid, a polyphosphoric acid and a salt.

Important features of this chitosan gel system are that: 1) it can be applied directly to bleeding fields; 2) it is applied as a transparent solution; 3) it quickly wets and adheres to tissue rapidly; 4) it demonstrates significantly faster bleeding control than the standard of care; 5) it is biocompatible; 6) it is a composition that promotes wound-healing and reduces scarring; 7) it can be applied quickly displacing blood and sealing injury, 8) it can be left in place or removed by suction, lavage or absorption without causing re-bleeding; 9) it can be administered so as to control bleeding without interfering with surgical field visualization or access; and 10) it is stable at 23±2° C. for at least 3 years.

DETAILED DESCRIPTION

The following description describes certain embodiments and is not to be taken in a limiting sense.

An aqueous chitosan gel system of novel non-scarring, non-interfering, transparent, stable, solubilized chitosan that controls bleeding is described herein. According to the invention the aqueous chitosan gel system is provided: comprising water, chitosan, an acid, a plasticizer, a rheology modifying agent, an antioxidant stabilizer an alcohol and a multivalent salt. Additional components may comprise a bifunctional organic acid, a trifunctional organic acid, a multi-functional organic acid, a phosphoric acid, a triphosphoric acid, a polyphosphoric acid and a salt.

The water fraction of the chitosan gel system is generally greater than 80% by weight of the system.

The chitosan weight fraction of the system is generally greater than 3% and less than 10%. Below pH 6.5, in the presence of an acid, the chitosan is water-soluble. By selection of the chitosan molecular weight and it's weight fraction the gel viscosity can be tuned to a desirable range. It needs to be viscous enough to be able to promote film-forming structures that resist collapse in oozing blood while it cannot be so viscous that it resists application pressure in deliver). The chitosan and acid composition provide muco-adhesive properties that are desirable for film forming properties combined with adhesion to tissue and subsequent promotion of hemostasis. The aqueous chitosan structures provide for clear transparent films that allow for visualization of underlying tissue.

A mono-functional organic acid is preferably used to dissolve chitosan and provide for strong mucoadhesion properties. Lactic acid and glycolic acids have minimal odor and are well tolerated against normal and injured tissue. The monofunctional acid should have minimal odor and be well tolerated against normal and injured tissue. A strongly volatile organic acid such as carbonic acid may be used to provide for rapid film forming characteristics.

A bi-functional and a tri-functional organic acid provide for assistance with solubilization of the chitosan as well as promotion of gelation due to formation of polyelectrolyte complexes.

A polyfunctional organic acid provides for promotion of gelation due to formation of polyelectrolyte complexes.

Phosphoric and triphosphoric acids are tolerated in low concentrations and provide for promotion of gelation due to formation of polyelectrolyte complexes.

Polyphosphoric acid is tolerated in low concentrations and provides for promotion of gelation due to formation of polyelectrolyte complexes.

A plasticizer provides for compliance of dried adhered film against tissue.

A rheology modifier provides for enhancement in gel flow and film forming characteristics when applied under shear to tissue.

An antioxidant stabilizer enhances shelf life characteristics and protects against degradation of the chitosan when exposed to heat or ionizing radiation exposure such as under gamma irradiation sterilization.

An alcohol enhances shelf-life and provides added stability against ionizing radiation exposure such as under gamma irradiation sterilization. An alcohol can be a helpful adjuvant in achieving hemostasis.

A multivalent salt assists with gelation and in the case of calcium can be a helpful adjuvant in achieving hemostasis.

A salt such as sodium chloride may be used for minor adjustment to electrolytic solution properties.

In one embodiment a chitosan or a biocompatible salt thereof is present in an amount of chitosan from 2.0% to 12.0% by weight.

The gel viscosity is preferably between 5,000 to 1,000,000 cP, is more preferably between 50,000 to 350,000 cP, and is most preferably between 75,000 to 250,000 cP. The gel viscosity is measured using a Brookfield DVII-Pro Digital viscometer with Small Sample Adapter and an LV-4 spindle. Measurements are made at 25±0.2° C. at a revolutions per minute (rpm) rate that is between 10% and 75% of the maximum viscometer strain rate (typically between 0.3 and 3.5 rpm).

In one embodiment an organic acid is used to solubilize the chitosan in water. The acid may be a monofunctional, a bifunctional or a trifunctional organic acid. Preferably a monofunctional organic acid is used for solubilization of the chitosan in the water. The monofunctional organic acid may include carbonic, lactic, glycolic and acetic acids. The monofunctional acid component may comprise 0.5% to 7% by weight of the gel. Lactic acid is a preferred monofunctional acid since it readily dissolves chitosan and provides for strong mucoadhesion properties. Carbonic, lactic acid and glycolic acids have minimal odor and are well tolerated against normal and injured tissue.

In one embodiment a difunctional or trifunctional organic acid is used to solubilize the chitosan in water and to promote gelation. The difunctional and trifunctional organic acids may improve gelation properties by formation of polyelectrolyte complexes with chitosan. The difunctional and trifunctional organic acids may include citric, succinic, malonic, adipic, tartaric and tannic acids. The difunctional and trifunctional acid components may comprise 0.0% to 5% by weight of the gel.

In one embodiment a polyfunctional organic acid is used to provide enhanced gelation properties to the chitosan in water. The polyfunctional organic acid may include polyacrylic acid, alginic acid, hyaluronic acid, carboxy methyl chitosan, carboxymethylcellulose and polyanhydroglucuronic acid. The polyfunctional organic acid may be present in 0.0-3% by weight of the gel.

In one embodiment an inorganic phosphoric, triphosphoric and polyphosphoric acids may be included to provide enhanced gelation properties. The inorganic acids may be present in 0.0-3% by weight of the gel.

In one embodiment, the composition comprises a chitosan plasticizer. The plasticizer may include sucrose, glycerol, sorbitol and mannitol, The plasticizer may be present in 0.0-5% by weight of gel.

In one embodiment, the composition comprises a rheology modifying agent. Rheology modifying agents may be dextran, hydroxy propyl cellulose, hydroxy propyl methyl cellulose, hydroxy ethyl cellulose, hydroxy propyl ethyl cellulose, polyethylene oxide, poloxamer, polyethylene glycol and polypropylene glycol, The poloxamer is preferably poloxamer 407. The rheology modifying agent comprises 0.5% to 5% by mass of the gel system.

In one embodiment the system contains an antioxidant stabilizer. The antioxidant may include methyl paraben, tannic acid, trolox, quercetin, catechin, glutathione, ferulic acid, carotenoid, proanthocyanidin, and ascorbic acid. The antioxidant comprises 0.1% to 2.5% by mass of the gel system.

In one embodiment the gel comprises an alcohol. The alcohol may include ethanol and isopropanol. The alcohol comprises 0.2% to 10% by mass of the gel system.

In one embodiment the gel comprises a multivalent salt. The multivalent salt may include $CaCl_2$, $Ca(NO_3)_2$, $Ca(SO_4)_2$, $BaCl_2$, $Ba(NO_3)_2$ and $Ba(SO_4)_2$. The multivalent salt comprises 0.1% to 0.5% by mass of the gel system.

In one embodiment the gel comprises approximately 3.25% (w/w) chitosan, approximately 2% (w/w) lactic acid, approximately 0.2% (w/w) methylparaben, approximately 0.5% (w/w) hydroxy propyl cellulose, approximately 0.2% (w/w) polyethylene oxide, approximately 0.2% (w/w) poloxamer 407, approximately 0.1% (w/w) polypropyleneglycol 2000, approximately 0.28% (w/w) $CaCl_2$, approximately 5% (w/w) ethanol and approximately 88.3% (w/w) water.

In another embodiment the gel comprises approximately 5.65% (w/w) chitosan, approximately 3.5% (w/w) lactic acid, approximately 1% (w/w) ascorbic acid, approximately 0.5% (w/w) hydroxy propyl cellulose, approximately 0.2% (w/w) polyethylene oxide, approximately 0.2% (w/w) poloxamer 407, approximately 0.1% (w/w) polypropyleneglycol 2000, approximately 0.31% (w/w) $CaCl_2$, approximately 5% (w/w) ethanol and approximately 83.5% (w/w) water.

Chitosan Gel System

The chitosan gel of this invention disclosure may be prepared with processes providing terminally sterilized, aseptic or non-sterile gel solutions.

In one embodiment the chitosan gels comprise an antimicrobial agent. The antimicrobial agent may include silver, chitosan derivatives (such as chitosan arginine and N-trimethyl chitosan) that are polycationic in the pH range 6.8-7.8, chlorhexidine gluconate, iodine and polyhexamethyl biguanide The invention further provides for a delivery device containing the chitosan gels of the invention. The delivery device may be selected from a group comprising a pipette, a syringe, a syrette, a suppository, a sponge, a patch, a cannula, a vial, a tube, a spray bottle or a spray can The invention further provides for tube directed delivery for topical, endoscopic or laparoscopic application to a bleeding surgical field. The tip of the tube may be conformed to provide optimal delivery of the gel to the surgical field. The tip configuration would allow provision of a ribbon profile, rectangular, circular, elliptical or any other tip opening for delivery of the gel to the surgical site.

The invention also provides the use of the chitosan gel system of the invention for control of bleeding or to facilitate or achieve hemostasis during or after, for example, sinus surgery, in ear nose and throat procedures, in oral and maxillofacial surgery, in orthopedic surgery, in urological surgery, in reconstructive surgery, in cosmetic surgery, in vascular surgery, in transplant surgery, in neurological surgery, in oncological resection surgery involving the biopsy and removal of tumors, and in gynecological surgery.

The present invention provides chitosan gel system of the invention that controls bleeding during and after surgery while supporting the wound healing process and without obscuring or interfering with the surgical field and thus allowing continued surgical access to the site. In particular, the present invention provides transparent chitosan gel preparations in combination with a gelling agent that when applied control bleeding by coating the surface of the injury allowing interaction between blood from the bleeding site and the chitosan which controls the bleeding while at the same time allowing visualization of the underlying wound surface and the occurrence or not of bleeding at that surface.

The invention provides a system that coats the injured area and adheres, remaining on the bleeding site allowing the polysaccharide to interact with components of the blood to accelerate the management of the bleeding.

The viscosity and tack of the chitosan gel are important functional elements for rapidly achieving hemostasis. The viscosity directly affects the cohesiveness of the gel and its ability to displace blood and remain intact at the bleeding surgical field, thus providing contact with the tissue beneath the blood. Too low a viscosity (below 1000 cps at 25° C.) would mean the gel would disperse in the blood before contacting the tissue, while too high a viscosity (>1,000,000 cps at 25° C.) would interfere with the ability of the gel to be delivered from the delivery device. The tack of the gel directly determines how well the gel will adhere to the tissue and hence how long it will be able to resist the direct flow of blood and provide opportunity for hemostasis. The viscosity modifier helps manage the viscosity of the final system formulation that is important for the function of the system.

Control of bleeding in a swine injury model of sinus bleeding has demonstrated that the chitosan gel systems are highly effective at quickly controlling sinus bleeding while maintaining the patency of the nasal cavity.

Rat and swine wound healing studies have also demonstrated that the chitosan gel systems in addition to controlling bleeding also promote the wound healing process and regeneration.

The system generally comprises components selected from a group consisting of a preservative, a moisturizer, a surfactant, a thickener, an emulsifier and an adhesive.

The invention provides a chitosan gel system in combination with a rheology modifying agent that reduces bleeding from nasal wounds when applied during surgery and supports the wound healing process.

The gel system may be used to reduce bleeding in a range of surgical processes or topical wounds.

The chitosan thereof may be present in the range of 2% to 12% (w/w) to provide the optimum bleeding control for the particular intended use of the gel.

The viscosity of the chitosan gel at low shear rate is preferably between 5,000 to 1,000,000 cP. The viscosity of the gel at low shear rate is more preferably between 50,000 to 350,000 cP. The viscosity of the gel at low shear rate is most preferably between 75,000 to 250,000 cP.

The viscosity of the gel is measured using a Brookfield DVII-Pro Digital viscometer with Small Sample Adapter and an LV-4 spindle or other suitable spindle. Measurements are made at 25±0.2° C. at a revolutions per minute (rpm) rate that is between 10% and 75% of the maximum viscometer strain rate (typically between 0.5 and 3.5 rpm).

The tack of the gel is measured using EN-1719:1998 [Tack measurement for pressure-sensitive adhesives—Determination of loop tack] with a 1"×7" Teflon™ loop at 23±2° C. and a crosshead speed of 5 mm/s. The tack of the chitosan gel is preferably greater than 65 mN, more preferably greater than 80 mN, and is most preferably greater than 90 mN.

In one embodiment, the components that make up the chitosan gel system for use on surgical wounds may be present in the system with the final concentrations 3.25% (w/w) chitosan, 2% (w/w) lactic acid, 0.2% (w/w) methylparaben, 0.5% (w/w) hydroxy propyl cellulose, 0.2% (w/w) polyethylene oxide, 0.2% (w/w) poloxamer 407, 0.1% (w/w) polypropyleneglycol 2000, 0.28% (w/w) $CaCl_2$, 5% (w/w) ethanol and 88.3% (w/w) water.

In another embodiment, the components that make up the chitosan gel system for use on surgical wounds may be present in the system with the final concentrations 5.65% (w/w) chitosan, 3.5% (w/w) lactic acid, 1% (w/w) ascorbic acid, 0.5% (w/w) hydroxy propyl cellulose, 0.2% (w/w) polyethylene oxide, 0.2% (w/w) poloxamer 407, 0.1% (w/w) polypropyleneglycol 2000, 0.31% (w/w) $CaCl_2$, 5% (w/w) ethanol and 83.5% (w/w) water.

The chitosan gel can be used in a terminally sterilized, aseptic or non-sterile format. Preferably the chitosan gel is prepared aseptically as this allows for enhanced hemostatic performance as well as extended shelf-life.

Aseptic preparation of the gel is performed by sterilization of individual dry (<5% w/w water) polymeric components by gamma irradiation or other appropriate sterilization procedure that causes insignificant chemical change. Aqueous soluble, low molecular weight, solid, low fractional weight percentage (≤0.2%) polymeric and liquid components or solutions may be sterilized by aqueous sterile filtration methods. The mixing formulation of the aqueous gel may be performed in a reactor that has been sterilized by autoclave or some other appropriate method of sterilization. The reactor is filled aseptically with its individual sterile components and these components are processed in the reactor into the aseptic aqueous chitosan gel. The aseptically prepared chitosan gel is then transferred aseptically to sterile syringes or other delivery receptacles that are aseptically packaged in sterile packaging. By sampling of filled final product receptacles, the aseptic nature of the product is validated and the product is available for aseptic release.

The concentration of the viscosity-modifying agent is suitably adjusted to allow for any decrease in viscosity during the sterilization process to give the optimum viscosity post sterilization for the intended use.

Typically, the water and other agents used to make the gel are purged of oxygen to enhance product shelf life.

The chitosan gel may be used to stop bleeding in ear nose and throat procedures as well as surgical procedures such as, for example, neurological, vascular, general reconstructive, oncological and gynecological procedures as well as topical uses of the composition.

The chitosan gel system may comprise an anti-microbial agent.

The chitosan gel system can be removed by suction, lavage, bioresorption, bioabsorption or biodegradation without causing rebleeding.

The chitosan gel system can be administered so as to control bleeding without interfering with surgical field visualization or access.

The chitosan gel composition may be administered from a delivery device selected from, for example, a syringe, a tube, a spray bottle or a spray can.

The invention further provides for tube directed delivery for topical, endoscopic or laparoscopic application to a bleeding surgical field. The tip of the tube may be conformed to provide optimal delivery of the gel to the surgical field. The tip configuration would allow provision of a ribbon profile, rectangular, circular, elliptical or any other to be delivered to the surgical site.

The gel system in its non-irradiated, aseptically manufactured form has shelf life when stored at 23±2° C. for at least 3 years.

BRIEF DESCRIPTION OF THE DRAWINGS

The invention will be more clearly understood from the following description of an embodiment thereof, given by way of example only, with reference to the accompanying drawings, in which.

DETAILED DESCRIPTION

Although the disclosure hereof is detailed and exact to enable those skilled in the art to practice the invention, the physical embodiments herein disclosed merely exemplify the invention that may be embodied in other ways. While the preferred embodiment has been described, the details may be changed without departing from the invention.

The chitosan gel composition includes a high molecular weight (HMW) chitosan. The weight average molecular weight (Mw) of the high molecular weight chitosan determined by gel permeation chromatography (GPC) was preferably between 300 and 2000 kDa with polydispersity index (Mw/Mn) ≤3, more preferably it was between 500 kDa and 1,500 kDa with polydispersity index ≤2.5 and most preferably it was between 750 to 1,250 kDa with polydispersity index ≤2. The chitosan gel composition may also include a low molecular weight (LMW) chitosan. The low molecular weight chitosan is ≤25% w/w of the sum of the weight of the high molecular weight and the low molecular weight chitosan components. Preferably the weight average molecular weight of the low molecular weight chitosan is between 5 and 70 kDa with polydispersity index ≤3, more preferably it is between 10 and 50 kDa with polydispersity index ≤2.5, and most preferably it is between 15 and 35 kDa with polydispersity index ≤2.

In the case of a fully bioabsorbable chitosan gel the percent degree of deacetylation is preferably between 20% and 40%. In the case of a dissolvable or otherwise removable chitosan gel, the percent degree of deacetylation is preferably ≥78%, more preferably ≥85% and most preferably ≥90%.

The HMW chitosan was Marinard Lot 158407AR with weight average molecular weight determined as 438,500 Da with polydispersity index of 1.59 and percentage degree of deacetylation of 86.5% (as determined by Miya's FTIR method: Miya, M., Iwamoto, R., Yoshikawa, S., and Seiichi, M., I. r. spectroscopic determination of CONH content in highly deacetylated chitosan Int. J. Biol.l Macromol., 1980. 2 (5): p. 323-324). The LMW chitosan was Primex Lot 21012 gamma irradiated from Mw 400 kDa to weight average molecular weight 39,188±2862 Da with polydispersity index of 1.7 and percentage degree of deacetylation of 78% (as determined by Miya's FTIR method). Lactic acid was from JT Baker, hydroxypropyl cellulose of molecular weight 370 kDa was from Spectrum Chemicals, poloxamer 407 (Pluronic F127) of molecular weight 12.5 kDa was from Spectrum Chemicals, polyethylene oxide of molecular weight 400 kDa was from Sigma Chemicals, polypropylene glycol of molecular weight 2000 was from Fluka, calcium chloride was from JT Baker, sodium chloride was from JT Baker, methyl paraben was from Sigma Chemicals, and ethanol was from Sigma Chemicals, ascorbic acid was from Sigma.

The present invention provides products and methods for controlling the bleeding from wounds such as those occurring during surgery without affecting access or visualization of the surgical site. Upon application of the chitosan gel system to the bleeding surgical site, the chitosan gel system adheres to and coats the immediate injury providing for the polysaccharide to both restrict and interact with blood flowing from injury. This interaction reduces the bleeding from the site by physical occlusion and by accelerating the hemostasis of the blood.

Most notably, the system of the present invention has shown beneficial qualities by successfully reducing bleeding quickly thus enabling the surgeon to continue the required procedure. Further notably the system stops the bleeding in a manner that allows continuation of the surgical procedure as the system functions without occluding the view of the surgical field. In demonstration of the applicability of this system to the general surgical field, this invention disclosure has chosen as its model the difficult surgical field of endoscopic sinus surgery within the nasal passage.

The present system provides advantages over other nasal hemostatic treatments not only in its speed to controlling bleeding for the surgeon but also in the lack of pain and discomfort experienced in use by the patient associated by other methods that employ packing or stent systems. A further advantage of this system is the support of the wound healing process by the gel system that is in contrast to other nasal bleeding treatments that can have unfavorable consequences on the wound healing process.

The present system provides the additional benefit over other systems when prepared aseptically in that it remains stable for an extended period (≥3 years) at room temperature maintaining its ability to provide visualization of the wound site after application of the gel.

EXAMPLE 1

Sinus Surgery Chitosan Hemostatic Gel

Two chitosan gels were prepared with compositions

| Chitosan Gel A | |
|---|---|
| Ingredients | Formulation (% (w/w)) |
| HMW Chitosan | 2.67 |
| LMW Chitosan | 0.58 |
| Lactic Acid | 2.0 |
| Methylparaben | 0.2 |
| Hydroxy propyl cellulose | 0.45 |
| Polyethylene Oxide | 0.18 |
| Poloxamer 407 | 0.18 |
| Polypropylene glycol 2000 | 0.1 |
| Calcium Chloride | 0.27 |
| Ethanol | 4.45 |
| Water | 89 |
| Sodium chloride | 0.0003 |

| Chitosan Gel B | |
|---|---|
| Ingredients | Formulation (% (w/w)) |
| HMW Chitosan | 5.0 |
| LMW Chitosan | 0.65 |
| Lactic Acid | 3.5 |
| Ascorbic acid | 1.0 |
| Hydroxy propyl cellulose | 0.5 |
| Polyethylene Oxide | 0.2 |
| Poloxamer 407 | 0.2 |
| Polypropylene glycol 2000 | 0.1 |
| Calcium Chloride | 0.31 |
| Ethanol | 5.0 |
| Water | 83.54 |
| Sodium chloride | 0.0003 |

Chitosan gel A was prepared without terminal sterilization while Chitosan gel B was terminally sterilized by gamma irradiation at 15 kGy, sufficient to produce a sterility assurance limit (SAL) of $10^{-6}$.

In this example, the chemical and physical properties of a non-aseptically manufactured chitosan aqueous gel that is not terminally sterilized by gamma irradiation will be considered substantially equivalent to the chemical and physical properties of an aseptically prepared aqueous gel. This is justifiable since gamma irradiation of aqueous polymeric gels at doses typically used for gamma sterilization (11-40 kGy) causes substantial polymer chain degradation while other forms of processing do not.

The viscosity of the material is suitable for dispensing through a nozzle or small orifice to the site of bleeding. The dispensing apparatus can be a syringe, a tube or any such similar device. In this example the gel was loaded into a syringe.

The viscosity of chitosan Gel A was determined using a Brookfield viscometer at 25° C. as 42,253±1683 cps. The viscosity of chitosan Gel B was determined using a Brookfield viscometer at 25° C. as greater than 2,000,000 cps without sterilization and 662,500 cps after 15 kGy gamma irradiation.

Figure 1:
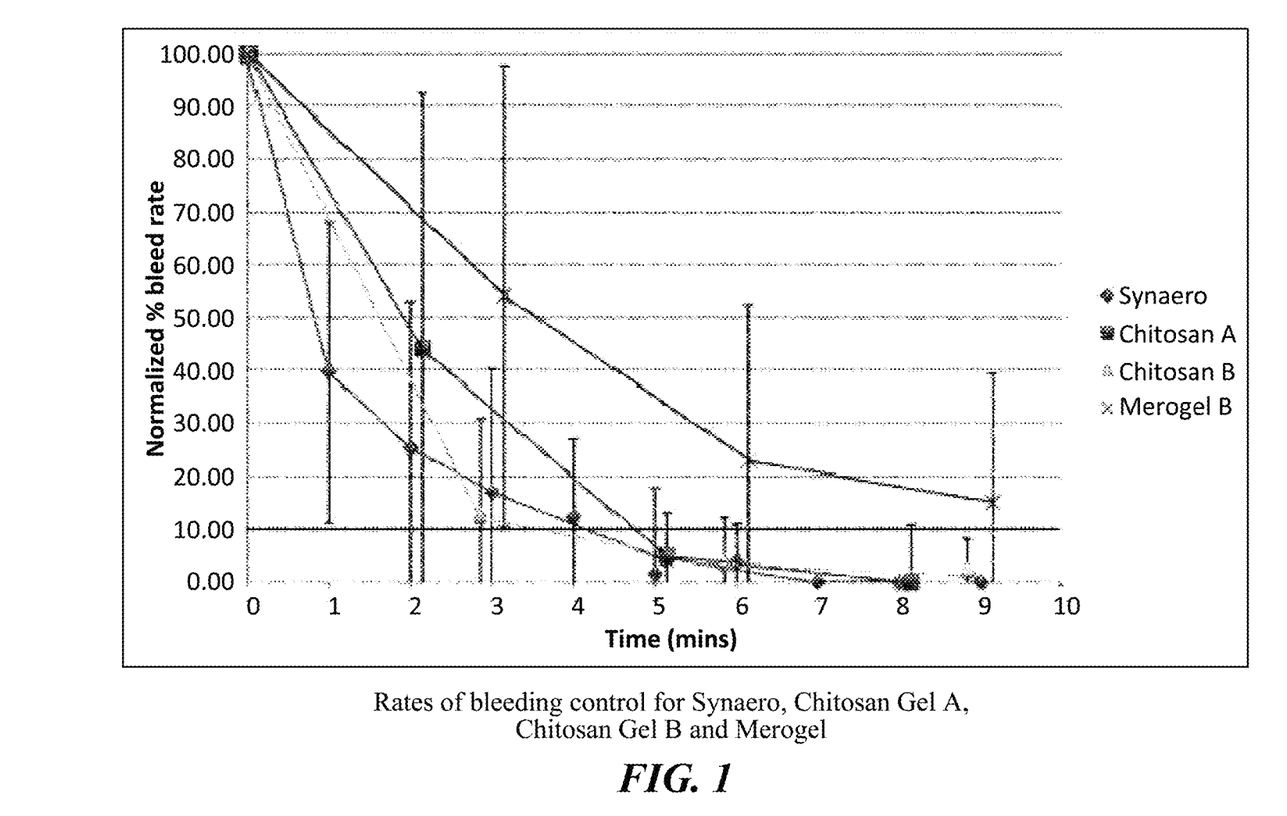
FIG. 1 is a graph of normalized % bleed rate (ordinate) plotted against time in minutes for control or test chitosan gel systems in a swine model of endoscopic surgical sinus bleeding. Merogel and Synaero commercial gels were used as controls in the study.

Epistaxis bleeding in the swine model was induced under anesthesia by bilateral mucosal stripping of the lateral nasal wall. Bleed-rates were measured by 20 second pre- and post-weighed gauze contact with freely bleeding sites. Initial bleed rates were targeted to be between 5 and 10 g/min. Actual initial bleed rates ranged between 2.0 and 20 g/min. The Normalized bleed rate is the initial rate and subsequent bleed rates at time t minutes for a given injury divided by the initial bleed rate. The gel was applied to swine nasal mucosa laceration injuries and successful hemostasis was achieved for both gamma and non-gamma irradiated chitosan gels. Application of the chitosan containing gel coated the surface of the injury, allowing interaction between the bleeding site and the chitosan. The bleeding control results are shown in FIG. 1 with controls of Merogel and HemCon polyanhydroglucuronate (Synaero™ Lot RD0610012) gels. There was 90% reduction in bleeding on average at >10 minutes, 4 minutes 5 seconds, 4 minutes 40 seconds, and 3 minutes 40 seconds for Merogel, Synaero, Chitosan Gel A and Chitosan Gel B respectively. The Synaero and Chitosan Gels were all effective in controlling bleeding with at least 90% reduction in bleeding in all three by 5 minutes. The Synaero gel was a non-transparent cream appearance that dried to an opaque film, whereas both Chitosan gels were clear liquids that dried to clear films. Chitosan Gel B had a red coloration. Both Chitosan Gels were adherent and coated vertical and inverted tissue surfaces. The animal group for Chitosan B was euthanized at the conclusion of the hemostatic testing. In the case of the Merogel, Synaero and Chitosan A, after seven days the animals were sacrificed and the injury sites evaluated for residual gel material, nasal passage patency, scarring, wound healing and inflammation. The Table I below lists the comparative results.

TABLE I

Comparative results

| Treatment Group | Residual Material | Nasal Patency | Scarring | Mucosal Healing | Inflammation |
|---|---|---|---|---|---|
| Chitosan A | No | Yes | No | Yes | Yes |
| Chitosan A | No | Yes | No | Yes | No |
| Chitosan A | No | Yes | No | Yes | No |
| Merogel | No | Yes | No | Yes | Yes |
| Merogel | No | Yes | No | Yes | No |
| Merogel | No | Yes | No | Yes | No |
| PAGA | No | Yes | No | Yes | No |
| PAGA | No | Yes | No | Yes | No |
| PAGA | No | Yes | No | Yes | No |

EXAMPLE 2

Stability of Chitosan Hemostatic Gel with and without Irradiation

Chitosan Gel C was prepared with the following composition.

| Ingredients | Formulation (% (w/w)) |
|---|---|
| HMW Chitosan | 2.65 |
| LMW Chitosan | 0.6 |
| Lactic Acid | 3.1 |
| Methylparaben | 0.2 |
| Hydroxy propyl cellulose | 0.44 |
| Polyethylene Oxide | 0.18 |
| Poloxamer F127 | 0.18 |
| Polypropylene glycol 2000 | 0.088 |
| Calcium Chloride | 0.27 |
| Ethanol | 4.42 |
| Water | 87.9 |
| Sodium chloride | 0.0003 |

The Chitosan Gel C of example 2 was sealed inside 10.0 ml syringes. The syringes were either not irradiated or they were exposed to electron beam irradiation or gamma irradiation. Brookfield viscometry at 25±0.2° C. using an LV4 spindle was used to determine change in viscosity of Chitosan Gel C following gamma irradiation or electron beam irradiation at doses typically used to sterilize medical devices. The results of testing are shown in Table 2.

TABLE 2

| Treatment | Gel Viscosity | % Change |
|---|---|---|
| None | 42,450 ± 500 | 0 |
| Gamma Irradiation 12-15 kGy | 425 ± 10 | −99% |
| Electron-beam irradiation 15 kGy | 385 ± 5 | −99% |

EXAMPLE 3

Stability of Chitosan Hemostatic Gel With and Without Irradiation for 66 Months at 23±2° C.

The syringes in Example 2 were stored at 23±2° C. for 66 months with regular examination. The A bubble of air (0.33±0.03 ml) with radius less than the syringe barrel radius (6.4±0.1 mm) was included inside each syringe so that relative rate of bubble travel at 23±2° C. through the gel column of length 39.5±0.5 mm could be monitored with syringe barrel positioned vertically. This provided a simple bubble point viscometer configuration to allow monitoring change in relative solution viscosity by determination of time of controlled distance travel in a vertical syringe barrel. At storage for 66 months at 23±2° C., the bubble time for travel of the bubble to ascend through chitosan solution of density near 0.98 g/cm$^3$ from base to top of syringe (39.5±0.5 mm) was 33.5±3.4 seconds for the non-irradiated sample and close to 2 seconds for the electron beam irradiated sample. Brookfield viscometry at 25±0.2° C. using an LV4 spindle was used to determine change in viscosity of irradiated and non-irradiated Chitosan Gel C after 66 months at 23±2° C. with results shown in Table 3.

TABLE 3

| Condition | Gel Viscosity (cps) | % Change |
|---|---|---|
| Baseline no irradiation | 42,450 | — |
| Baseline Electron-beam irradiation 15 kGy | 385 | — |
| 66 months no irradiation | 12,000 | −70% |
| 66 months Electron-beam irradiation 15 kGy | 400 | +4% |

Figure 2:
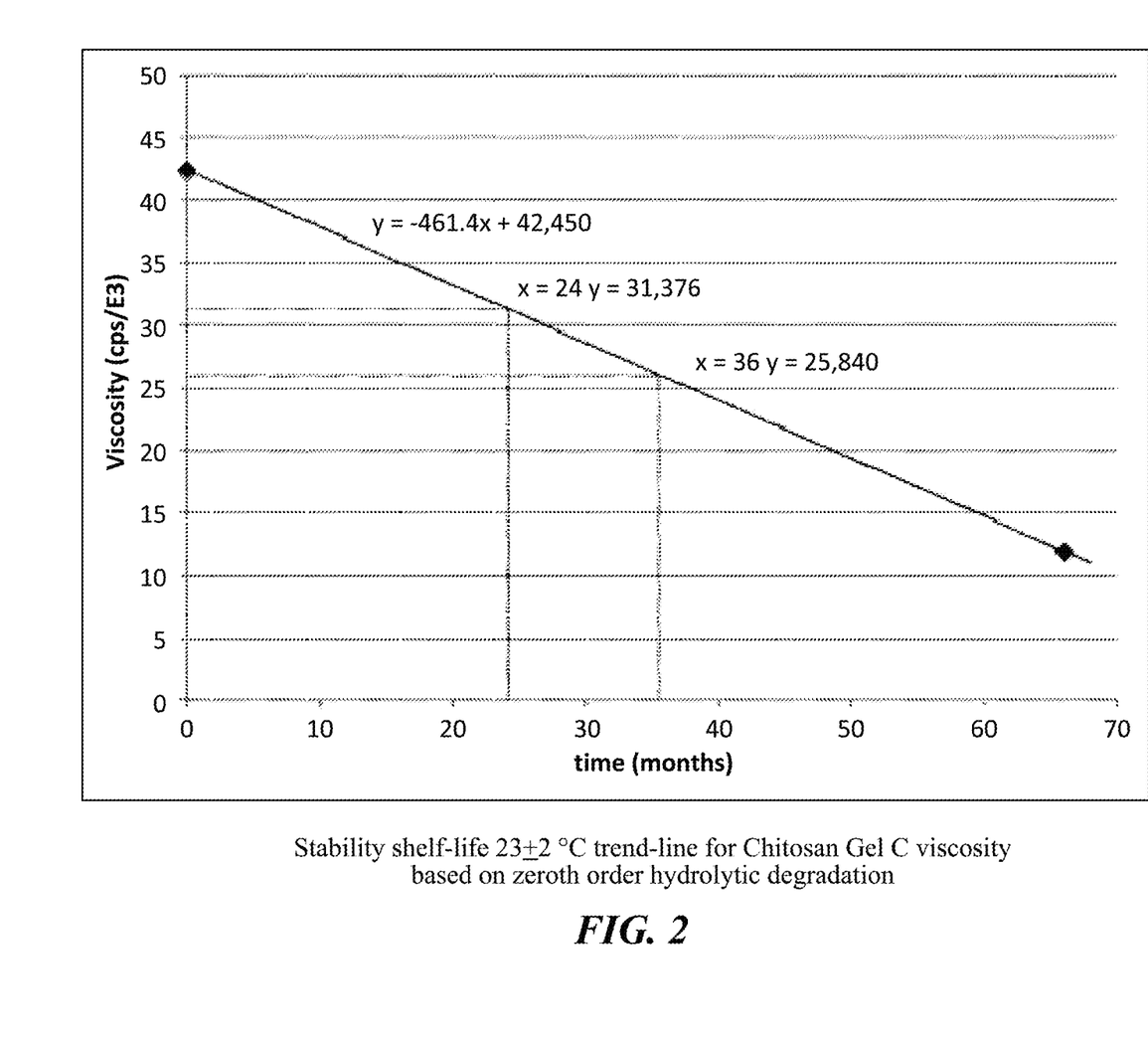
FIG. 2 shows stability shelf-life at 23±2° C. trend-line for Chitosan Gel C viscosity based on zeroth order hydrolytic degradation.

From Table 3 and FIG. 2.

Embodiments of the present invention include a clear gel system aqueous composition comprising chitosan, a monofunctional organic acid, a rheology modifying agent, an antioxidant stabilizer, an alcohol and a multivalent salt that is stable for a period up to three years at about 23° C., that can be applied directly to bleeding wounds in surgery, to displace the blood, and adhere to tissue to quickly control the bleeding without obscuring or interfering with access to the surgical site and can be removed without rebleeding. Such gel systems may include one or more of the following: chitosan present in an amount of about 2% to about 12% (w/w); a monofunctional organic acid selected from the group comprising lactic, glycolic, and carbonic acids; a monofunctional organic acid present in an amount of about 0.5% to about 7% (w/w), a bifunctional, trifunctional and polyfunctional organic acids present at up to 5.0% by weight of the gel; an inorganic phosphoric, triphosphoric and/or polyphosphoric acid present at up to 3.0% by weight of the gel; a plasticizer present at up to 5.0% by weight of the gel; a rheology modifying agent selected from a group comprising hydroxypropylcellulose, polyethylene oxide, poloxamer 407, polyethylene glycol, and polypropylene glycol 2000; a rheology modifying agent comprising about 0.5% to 5% by mass of the gel system; an antioxidant stabilizer selected from a group comprising methyl paraben, tannic acid, trolox, quercetin, catechin, glutathione, ferulic acid, carotenoid, proanthocyanidin and ascorbic acid; an antioxidant stabilizer present in an amount of about 0.1% to about 2.5% (w/w); a multivalent salt; a multivalent salt selected from the group comprising $CaCl_2$, $Ca(NO_3)_2$, $Ca(SO_4)_2$, $BaCl_2$, $Ba(NO_3)_2$ and $Ba(SO_4)_2$; a multivalent salt present in an amount of about 0.1% to about 0.5% (w/w); an alcohol selected from the group comprising ethanol and isopropanol; an alcohol present in an amount of about 0.2% to about 10% (w/w); a premixed gel composition for delivery from a single syringe; a gel system having a viscosity of the gel from 5,000 to 1,000,000 cP at 25° C., 50,000 to 350,000 cP at 25° C., or 75,000 to 250,000 cP at 25° C.; a gel system comprising an anti-microbial agent; an anti-microbial agent selected from the group comprising silver, chitosan derivatives that are polycationic between pH 6.8-7.8, chlorhexidine gluconate, iodine and polyhexamethyl biguanide, a gel system removable by dissolution by surgical flushing (lavage); a gel system that can remain in place for removal by dissolution, bioresorption or by bioabsorption processes without further intervention; a gel system that may be applied to complex geometries including an inverted space; and an antimicrobial gel system.

Embodiments of the present invention include an aqueous gel system comprising chitosan, a monofunctional organic acid, a rheology modifying agent, an antioxidant stabilizer, an alcohol and a multivalent salt. Such gel systems may include one or more of the following: chitosan present in an amount of about 2% to about 12% (w/w); a monofunctional organic acid selected from the group comprising lactic, glycolic and carbonic acids; a monofunctional organic acid present in an amount of about 0.5% to about 7% (w/w); a bifunctional, trifunctional and polyfunctional organic acids present at up to 5.0% by weight of the gel; an inorganic phosphoric, triphosphoric, and polyphosphoric acids present at up to 3.0% by weight of the gel; a plasticizer present at up to 5.0% by weight of the gel; a rheology modifying agent selected from a group comprising hydroxypropylcellulose, polyethylene oxide, poloxamer 407, polyethylene glyclol, and polypropylene glycol 2000; a rheology modifying agent comprising about 0.5% to 5% by mass of the gel system; an antioxidant stabilizer selected from a group comprising methyl paraben, tannic acid, trolox, quercetin, catechin, glutathione, ferulic acid, carotenoid, proanthocyanidin, and ascorbic acid; an antioxidant stabilizer present in an amount of about 0.1% to about 2.5% (w/w); a multivalent salt; a multivalent salt selected from a group comprising $CaCl_2$, $Ca(NO_3)_2$, $Ca(SO_4)_2$, $BaCl_2$, $Ba(NO_3)_2$ and $Ba(SO_4)_2$; a multivalent salt present in an amount of about 0.1% to about 0.5% (w/w); an alcohol selected from the group comprising ethanol and isopropanol; an alcohol present in an amount of about 0.2% to about 10% (w/w); a premixed gel composition for delivery from a single syringe; a gel system having a viscosity of the gel from 5,000 to 1,000,000 cP at 25° C., 50,000 to 350,000 cP at 25° C., or 75,000 to 250,000 cP at 25° C.; an anti-microbial agent; an anti-microbial agent selected from the group comprising silver, chitosan derivatives that are polycationic between pH 6.8-7.8, chlorhexidine gluconate, iodine and polyhexamethyl biguanide; a gel system removable by dissolution by surgical flushing (lavage); a gel system that can remain in place for removal by dissolution, bioresorption or by bioabsorption processes without further intervention; a gel system that may be applied to complex geometries including an inverted space; an antimicrobial gel system; a tack greater than 65 mN, greater than 80 mN, or greater than 95 mN.

Further embodiments of the present invention include use of any gel system described herein to control bleeding or facilitate hemostasis during or after sinus surgery, in ear nose and throat procedures, in oral and maxillofacial surgery, in orthopedic surgery, in urological surgery, in reconstructive surgery, in cosmetic surgery, in vascular surgery, in transplant surgery, in neurological surgery, in oncological resection surgery involving the biopsy and removal of tumors, and in gynecological surgery, and for general topical bleeding.

CONCLUSIONS

The herein described, easily administered, stable, clear chitosan gel system is readily administered to bleeding surgical fields to displace blood and to adhere to tissue to effectively control bleeding, to promote wound healing with reduced scarring, to allow visualization and access to the same surgical fields and can be removed subsequently without rebleeding by saline lavage.

The invention is not limited to the embodiments herein before described which may be varied in detail.

REFERENCES

1. Valentine, R., P. J. Wormald, and R. Sindwani, Advances in absorbable biomaterials and nasal packing. Otolaryngol Clin North Am, 2009. 42 (5): p. 813-28, ix.
2. Virgin, F. W., B. S. Bleier, and B. A. Woodworth, Evolving materials and techniques for endoscopic sinus surgery. Otolaryngol Clin North Am, 2010. 43 (3): p. 653-72, xi.
3. Ogle, O. E. and H. Dym, Surgery of the Nose and Paranasal Sinuses: Principles and Concepts. Oral and Maxillofacial Surgery Clinics of North America, 2012. 24 (2): p. xiii-xiv.
4. Palmer, O., J. A. Moche, and S. Matthews, Endoscopic Surgery of the Nose and Paranasal Sinus. Oral and Maxillofacial Surgery Clinics of North America, 2012. 24 (2): p. 275-283.
5. Bugten, V., et al., Effects of nonabsorbable packing in middle meatus after sinus surgery. Laryngoscope, 2006. 116 (1): p. 83-8.
6. Chandra, R. K. and R. C. Kern, Advantages and disadvantages of topical packing in endoscopic sinus surgery. Curr Opin Otolaryngol Head Neck Surg, 2004. 12 (1): p. 21-6.
7. Huggins, S., Control of hemorrhage in otorhinolaryngologic surgery with oxidized regenerated cellulose. Eye Ear Nose Throat Mon, 1969. 48 (7): p. 420-3.
8. Shaw, C. L., et al., Effect of packing on nasal mucosa of sheep. J Laryngol Otol, 2000. 114 (7): p. 506-9.
9. von Schoenberg, M., P. Robinson, and R. Ryan, Nasal packing after routine nasal surgery—is it justified? J Laryngol Otol, 1993. 107 (10): p. 902-5.
10. Chandra, R. K., et al., Long-term effects of FloSeal packing after endoscopic sinus surgery. Am J Rhinol, 2005. 19 (3): p. 240-3.
11. Chandra, R. K., D. B. Conley, and R. C. Kern, The effect of FloSeal on mucosal healing after endoscopic sinus surgery: a comparison with thrombin-soaked gelatin foam. Am J Rhinol, 2003. 17 (1): p. 51-5.
12. Frenkiel, S., M. Y. Desrosiers, and D. Nachtigal, Use of hylan B gel as a wound dressing after endoscopic sinus surgery. J Otolaryngol, 2002. 31 Suppl 1: p. S41-4.
13. Karkos, P. D., et al., Day-case endoscopic sinus surgery using dissolvable haemostatic nasal packs: a pilot study. Eur Arch Otorhinolaryngol, 2007. 264 (10): p. 1171-4.
14. Maccabee, M. S., D. R. Trune, and P. H. Hwang, Effects of topically applied biomaterials on paranasal sinus mucosal healing. Am J Rhinol, 2003. 17 (4): p. 203-7.

15. Pomerantz, J. and J. M. Dutton, Platelet gel for endoscopic sinus surgery. Ann Otol Rhinol Laryngol, 2005. 114 (9); p. 699-704.

16. Woodworth, B. A., et al., A gelatin-thrombin matrix for hemostasis after endoscopic sinus surgery. Am J Otolaryngol, 2009. 30 (1): p. 49-53.

17. Wormald, P. J., et al., A prospective single-blind randomized controlled study of use of hyaluronic acid nasal packs in patients after endoscopic sinus surgery. Am J Rhinol, 2006. 20 (1): p. 7-10.

18. Foster, J., Bioadhesives as Surgical Sealants: A Review, in Bioadhesion and Biomimetics: From Nature to Applications. CRC Press, 2015. VitalBook file., H. Bianco-Peled and M. Davidovich-Pinhas, Editors. 2015, CRC Press: Boca Raton, Fla. 33487-2742. p. 219.

19. Levi, M. and T. van der Poll, Two-way interactions between inflammation and coagulation. Trends Cardiovasc Med, 2005. 15 (7): p. 254-9.

20. Levi, M., T. van der Poll, and H. R. Buller, Bidirectional relation between inflammation and coagulation. Circulation, 2004. 109 (22): p. 2698-704.

The invention claimed is:

1. An aqueous gel comprising:
water in an amount greater than about 88% (w/w);
chitosan in an amount of about 3% (w/w);
an acid component including one or more of a monofunctional organic acid in an amount of about 0.5% to about 7% (w/w), a difunctional or trifunctional organic acid in an amount up to about 5% (w/w), a polyfunctional organic acid in an amount up to about 3% (w/w), or an inorganic phosphoric, triphosphoric, or polyphosphoric acid in an amount up to about 3% (w/w), and wherein lactic acid, a monofunctional organic acid, is included in an amount of about 2% (w/w);
a rheology modifying agent including hydroxyl propyl methyl cellulose in an amount of about 0.5% (w/w), polyethylene oxide in an amount of about 0.2% (w/w), poloxamer in an amount of about 0.2% (w/w), and polypropylene glycol in an amount of about 0.1% (w/w);
an antioxidant stabilizer in an amount of about 0.1% to about 2.5% (w/w), wherein said antioxidant stabilizer is selected from the group consisting of methylparaben, tannic acid, trolox, quercetin, catechin, glutathione, ferulic acid, carotenoid, proanthocyanidin, and ascorbic acid, and including methylparaben in an amount of about 0.2%;
an alcohol in an amount of about 0.2% to about 10% (w/w), and including ethanol in an amount of about 5% (w/w); and
a multi-valent salt in an amount of about 0.1% to about 0.5% (w/w), and including $CaCl_2$ in an amount of about 0.3% (w/w).

2. The aqueous gel of claim 1, wherein the aqueous gel is at least one of clear and transparent.

3. The aqueous gel of claim 1, wherein the aqueous gel is stable for a period up to three years at about 23° C.

4. The aqueous gel of claim 1, further comprising at least one of a plasticizer in an amount up to about 5% (w/w) or an anti-microbial agent.

5. The aqueous gel of claim 1, wherein the aqueous gel is bioabsorbable and the chitosan has a percent degree of deacetylation between 20% and 40%.

6. The aqueous gel of claim 1, wherein the aqueous gel is removable and the chitosan has a percent degree of deacetylation greater than about 78%.

7. An aqueous gel comprising:
water in an amount greater than about 83.5% (w/w);
chitosan in an amount of about 5.7% (w/w);
an acid component including one or more of a monofunctional organic acid in an amount of about 0.5% to about 7% (w/w), a difunctional or trifunctional organic acid in an amount up to about 5% (w/w), a polyfunctional organic acid in an amount up to about 3% (w/w), or an inorganic phosphoric, triphosphoric, or polyphosphoric acid in an amount up to about 3% (w/w), and wherein lactic acid, a monofunctional organic acid, is included in an amount of about 3.5% (w/w);
a rheology modifying agent including hydroxyl propyl methyl cellulose in an amount of about 0.5% (w/w), polyethylene oxide in an amount of about 0.2% (w/w), poloxamer in an amount of about 0.2% (w/w), and polypropylene glycol in an amount of about 0.1% (w/w);
ascorbic acid in an amount of about 1% (w/w);
an alcohol in an amount of about 0.2% to about 10% (w/w), and including ethanol in an amount of about 5% (w/w); and
a multi-valent salt in an amount of about 0.1% to about 0.5% (w/w), and including $CaCl_2$ in an amount of about 0.3% (w/w).

8. The aqueous gel of claim 7, wherein the aqueous gel is at least one of clear and transparent.

9. The aqueous gel of claim 7, wherein the aqueous gel is stable for a period up to three years at about 23° C.

10. The aqueous gel of claim 7, further comprising at least one of a plasticizer in an amount up to about 5% (w/w) or an anti-microbial agent.

11. The aqueous gel of claim 7, wherein the aqueous gel is bioabsorbable and the chitosan has a percent degree of deacetylation between 20% and 40%.

12. The aqueous gel of claim 7, wherein the aqueous gel is removable and the chitosan has a percent degree of deacetylation greater than about 78%.

13. An aqueous gel comprising:
water in an amount greater than about 80% (w/w);
chitosan in an amount of about 2% to about 12% (w/w);
an acid component including one or more of a monofunctional organic acid in an amount of about 0.5% to about 7% (w/w), a difunctional or trifunctional organic acid in an amount up to about 5% (w/w), a polyfunctional organic acid in an amount up to about 3% (w/w), or an inorganic phosphoric, triphosphoric, or polyphosphoric acid in an amount up to about 3% (w/w);
a rheology modifying agent in an amount of about 0.5% to about 5% (w/w);
an antioxidant stabilizer in an amount of about 0.1% to about 2.5% (w/w), wherein said antioxidant stabilizer is selected from the group consisting of methylparaben, tannic acid, trolox, quercetin, catechin, glutathione, ferulic acid, carotenoid, proanthocyanidin, and ascorbic acid;
an alcohol in an amount of about 0.2% to about 10% (w/w);
a multi-valent salt in an amount of about 0.1% to about 0.5% (w/w); and
an anti-microbial agent, wherein the antimicrobial agent is selected from the group consisting of silver, chitosan derivatives that are polycationic between pH 6.8-7.8, chlorhexidine gluconate, iodine and polyhexamethyl biguanide.

14. The aqueous gel of claim 13, wherein the aqueous gel is at least one of clear and transparent.

15. The aqueous gel of claim 13, wherein the aqueous gel is stable for a period up to three years at about 23° C.

16. The aqueous gel of claim 13, further comprising at least one of a plasticizer in an amount up to about 5% (w/w) or an anti-microbial agent.

17. The aqueous gel of claim 13, wherein the aqueous gel is bioabsorbable and the chitosan has a percent degree of deacetylation between 20% and 40%.

18. The aqueous gel of claim 13, wherein the aqueous gel is removable and the chitosan has a percent degree of deacetylation greater than about 78%.

19. A surgical method comprising applying to an injury an aqueous gel comprising:
   water in an amount greater than about 88% (w/w);
   chitosan in an amount of about 3% (w/w);
   an acid component including one or more of a monofunctional organic acid in an amount of about 0.5% to about 7% (w/w), a difunctional or trifunctional organic acid in an amount up to about 5% (w/w), a polyfunctional organic acid in an amount up to about 3% (w/w), or an inorganic phosphoric, triphosphoric or polyphosphoric acid in an amount up to about 3% (w/w), and wherein lactic acid, a monofunctional organic acid, is included in an amount of about 2% (w/w);
   a rheology modifying agent including hydroxyl propyl methyl cellulose in an amount of about 0.5% (w/w), polyethylene oxide in an amount of about 0.2% (w/w), poloxamer in an amount of about 0.2% (w/w, and polypropylene glycol in an amount of about 0.1% (w/w);
   an antioxidant stabilizer in an amount of about 0.1% to about 2.5% (w/w), wherein said antioxidant stabilizer is selected from the group consisting of methylparaben, tannic acid, trolox, quercetin, catechin, glutathione, ferulic acid, carotenoid, proanthocyanidin, and ascorbic acid, and including methylparaben in an amount of about 0.2%;
   an alcohol in an amount of about 0.2% to about 10% (w/w), and including ethanol in an amount of about 5% (w/w); and
   a multi-valent salt in an amount of about 0.1% to about 0.5% (w/w), and including $CaCl_2$ in an amount of about 0.3% (w/w), to control bleeding or facilitate hemostasis during or after one or more of sinus surgery, ear nose and throat procedures, oral and maxillofacial surgery, orthopedic surgery, urological surgery, reconstructive surgery, cosmetic surgery, vascular surgery, transplant surgery, neurological surgery, oncological resection surgery involving the biopsy and removal of tumors, gynecological surgery, and general topical bleeding.

20. The method of claim 19, wherein the chitosan interacts with components of blood in the injury to control bleeding and facilitate hemostasis.

21. The method of claim 19, further comprising allowing bioabsorption of the aqueous gel, wherein the chitosan has a percent degree of deacetylation between 20% and 40%.

22. The method of claim 19, further comprising removing the aqueous gel from the injury, wherein the chitosan has a percent degree of deacetylation greater than about 78%.

23. A surgical method comprising applying to an injury an aqueous gel comprising
   water in an amount greater than about 83.5% (w/w);
   chitosan in an amount of about 5.7% (w/w);
   an acid component including one or more of a monofunctional organic acid in an amount of about 0.5% to about 7% (w/w), a difunctional or trifunctional organic acid in an amount up to about 5% (w/w), a polyfunctional organic acid in an amount up to about 3% (w/w), or an inorganic phosphoric, triphosphoric, or polyphosphoric acid in an amount up to about 3% (w/w), and wherein lactic acid, a monofunctional organic acid, is included in an amount of about 3.5% (w/w);
   a rheology modifying agent including hydroxyl propyl methyl cellulose in an amount of about 0.5% (w/w), polyethylene oxide in an amount of about 0.2% (w/w), poloxamer in an amount of about 0.2% (w/w), and polypropylene glycol in an amount of about 0.1% (w/w);
   ascorbic acid in an amount of about 1% (w/w);
   an alcohol in an amount of about 0.2% to about 10% (w/w), and including ethanol in an amount of about 5% (w/w); and
   a multi-valent salt in an amount of about 0.1% to about 0.5% (w/w), and including $CaCl_2$ in an amount of about 0.3% (w/w), to control bleeding or facilitate hemostasis during or after one or more of sinus surgery, ear nose and throat procedures, oral and maxillofacial surgery, orthopedic surgery, urological surgery, reconstructive surgery, cosmetic surgery, vascular surgery, transplant surgery, neurological surgery, oncological resection surgery involving the biopsy and removal of tumors, gynecological surgery, and general topical bleeding.

24. The method of claim 23, wherein the chitosan interacts with components of blood in the injury to control bleeding and facilitate hemostasis.

25. The method of claim 23, further comprising allowing bioabsorption of the aqueous gel, wherein the chitosan has a percent degree of deacetylation between 20% and 40%.

26. The method of claim 23, further comprising removing the aqueous gel from the injury, wherein the chitosan has a percent degree of deacetylation greater than about 78%.

27. A surgical method comprising applying to an injury an aqueous gel comprising:
   water in an amount greater than about 80% (w/w);
   chitosan in an amount of about 2% to about 12% (w/w),
   an acid component including one or more of a monofunctional organic acid in an amount of about 0.5% to about 7% (w/w) a difunctional or trifunctional organic acid in an amount up to about 5% (w/w), a polyfunctional organic acid in an amount up to about 3% (w/w), or an inorganic phosphoric, triphosphoric, or polyphosphoric acid in an amount up to about 3% (w/w);
   a rheology modifying agent in an amount of about 0.5% to about 5% (w/w);
   an antioxidant stabilizer in an amount of about 0.1% to about 2.5% (w/w), wherein said antioxidant stabilizer is selected from the group consisting of methylparaben, tannic acid, trolox, quercetin, catechin, glutathione, ferulic acid, carotenoid, proanthocyanidin, and ascorbic acid;
   an alcohol in an amount of about 0.2% to about 10% (w/w);
   a multi-valent salt in an amount of about 0.1% to about 0.5% (w/w); and
   an anti-microbial agent, wherein the antimicrobial agent is selected from the group consisting of silver, chitosan derivatives that are polycationic between pH 6.8-7.8, chlorhexidine gluconate, iodine and polyhexamethyl biguanide, to control bleeding or facilitate hemostasis during or after one or more of sinus surgery, ear nose and throat procedures, oral and maxillofacial surgery, orthopedic surgery, urological surgery, reconstructive surgery, cosmetic surgery, vascular surgery, transplant surgery, neurological surgery, oncological resection surgery involving the biopsy and removal of tumors, gynecological surgery, and general topical bleeding.

28. The method of claim 27, wherein the chitosan interacts with components of blood in the injury to control bleeding and facilitate hemostasis.

29. The method of claim 27, further comprising allowing bioabsorption of the aqueous gel, wherein the chitosan has a percent degree of deacetylation between 20% and 40%.

30. The method of claim 27, further comprising removing the aqueous gel from the injury, wherein the chitosan has a percent degree of deacetylation greater than about 78%.

* * * * *

UNITED STATES PATENT AND TRADEMARK OFFICE
CERTIFICATE OF CORRECTION

Page 1 of 1

PATENT NO. : 11,160,901 B2
APPLICATION NO. : 15/565388
DATED : November 2, 2021
INVENTOR(S) : Maggie Bush et al.

It is certified that error appears in the above-identified patent and that said Letters Patent is hereby corrected as shown below:

In the Claims

Column 17, Claim 19, Line 28:
"amount of about 0.2% (w/w," should read: --amount of about 0.2% (w/w),--.

Column 17, Claim 23, Line 61:
"aqueous gel comprising" should read: --aqueous gel comprising:--.

Column 18, Claim 27, Line 38:
"to about 12% (w/w)," should read: --to about 12% (w/w);--.

Signed and Sealed this
Fourteenth Day of March, 2023

Katherine Kelly Vidal
*Director of the United States Patent and Trademark Office*